(12) United States Patent
Sangiovani

(10) Patent No.: US 8,474,250 B2
(45) Date of Patent: Jul. 2, 2013

(54) DEVICE AND METHOD FOR THE REDUCTION OF EMISSIONS

(75) Inventor: Sergio Varkala Sangiovani, Santana (BR)

(73) Assignee: Sabertec L.L.C., Austin, TX (US)

( * ) Notice: Subject to any disclaimer, the term of this patent is extended or adjusted under 35 U.S.C. 154(b) by 1 day.

(21) Appl. No.: 12/845,345

(22) Filed: Jul. 28, 2010

(65) Prior Publication Data

US 2010/0307134 A1    Dec. 9, 2010

Related U.S. Application Data

(63) Continuation of application No. 11/743,765, filed on May 3, 2007, now abandoned.

(51) Int. Cl.
F01N 3/02 (2006.01)
F01N 3/00 (2006.01)
F01N 1/24 (2006.01)
H05K 5/00 (2006.01)

(52) U.S. Cl.
USPC ............... 60/311; 60/274; 181/151; 181/256

(58) Field of Classification Search
USPC ................ 60/274, 297, 299, 311; 181/151, 181/212, 228, 256
See application file for complete search history.

(56) References Cited

U.S. PATENT DOCUMENTS

| | | |
|---|---|---|
| 3,114,617 A | 12/1963 | Rowe et al. |
| 3,376,695 A | 4/1968 | Muckley |
| 3,406,501 A | 10/1968 | Watkins |
| 3,521,429 A | 7/1970 | Leffler |
| 3,633,343 A | 1/1972 | Mark |
| 3,819,334 A | 6/1974 | Yoshida et al. |
| 3,827,562 A | 8/1974 | Esmond |
| 3,871,850 A | 3/1975 | Lenane |
| 3,879,943 A | 4/1975 | Konig |
| 3,954,618 A | 5/1976 | Strauss |
| 4,297,116 A | 10/1981 | Cusick |
| 4,355,504 A | 10/1982 | Liu et al. |
| 4,469,079 A | 9/1984 | Cook |

(Continued)

FOREIGN PATENT DOCUMENTS

| | | |
|---|---|---|
| DE | 2748352 A1 | 5/1979 |
| DE | 3815148 A1 | 11/1989 |

(Continued)

OTHER PUBLICATIONS

Goto et al., English Abstract of JP 2003-336517 A, Nov. 28, 2003.*

(Continued)

*Primary Examiner* — Kenneth Bomberg
*Assistant Examiner* — Audrey K Bradley
(74) *Attorney, Agent, or Firm* — Alston & Bird LLP

(57) ABSTRACT

An emission reduction device which may be removably affixed to an engine's exhaust system. The device comprises a cylindrical carcass with a beveled opening in a diagonal line in its proximal part. A bobbin is affixed in the distal portion of the carcass. A cylindrical-shaped fibrous blanket may be inserted in the carcass and the fibrous blanket may be wrapped in a wire mesh. A second fiber mesh formed into a cone may be removably inserted in the cylindrical-shaped fibrous blanket with the larger diameter of the cone positioned proximally.

27 Claims, 7 Drawing Sheets

U.S. PATENT DOCUMENTS

| | | | |
|---|---|---|---|
| 4,478,618 | A | 10/1984 | Bly et al. |
| 4,576,799 | A | 3/1986 | Worner et al. |
| 4,706,454 | A | 11/1987 | Smith et al. |
| 4,829,766 | A | 5/1989 | Henkel |
| 5,138,836 | A | 8/1992 | Pfister |
| 5,139,107 | A | 8/1992 | Nagai |
| 5,205,850 | A | 4/1993 | Jenrich et al. |
| 5,238,472 | A | 8/1993 | Pfister et al. |
| 5,246,472 | A | 9/1993 | Herman et al. |
| 5,248,481 | A | 9/1993 | Bloom et al. |
| 5,248,482 | A | 9/1993 | Bloom |
| 5,258,164 | A | 11/1993 | Bloom et al. |
| 5,293,742 | A | 3/1994 | Gillingham et al. |
| 5,298,046 | A | 3/1994 | Peisert |
| 5,376,341 | A | 12/1994 | Gulati |
| 5,423,904 | A | 6/1995 | Dasgupta |
| 5,457,749 | A | 10/1995 | Cain et al. |
| 5,830,250 | A | 11/1998 | Shirk et al. |
| D410,010 | S | 5/1999 | Gieseke et al. |
| 6,013,118 | A | 1/2000 | Matsunuma et al. |
| 6,148,955 | A | 11/2000 | Wolf et al. |
| 6,228,261 | B1 | 5/2001 | Grangeon et al. |
| 6,284,201 | B1 | 9/2001 | Buck |
| 6,334,881 | B1 | 1/2002 | Giannetta et al. |
| 6,464,744 | B2 | 10/2002 | Cutler et al. |
| 6,474,319 | B1 | 11/2002 | Hough et al. |
| 6,767,378 | B2 | 7/2004 | Nishiyama et al. |
| 6,835,224 | B2 | 12/2004 | Cheng |
| 7,025,797 | B2 | 4/2006 | Zettel |
| D523,543 | S | 6/2006 | Komori et al. |
| 7,056,365 | B2 | 6/2006 | Ichikawa et al. |
| 7,452,831 | B2 | 11/2008 | Yamada et al. |
| 2004/0128964 | A1 | 7/2004 | Cheng |
| 2005/0109023 | A1 | 5/2005 | Kudo et al. |
| 2007/0012006 | A1 | 1/2007 | Sangiovani |

FOREIGN PATENT DOCUMENTS

| | | | |
|---|---|---|---|
| EP | 1515011 A1 | | 3/2005 |
| EP | 1611935 A1 | | 1/2006 |
| EP | 1544426 B1 | | 1/2008 |
| GB | 2163969 A | | 3/1986 |
| GB | 2163969 A | | 12/1986 |
| JP | 2000-248920 A | | 9/2000 |
| JP | 2000248920 A | * | 9/2000 |
| JP | 2003-336517 A | | 11/2003 |
| JP | 2003336517 A | * | 11/2003 |
| WO | WO 93/25998 | | 12/1993 |
| WO | WO-93/25998 A1 | | 12/1993 |

OTHER PUBLICATIONS

Kuroki, English Abstract of JP 2000-248920 A, Sep. 12, 2000.*
Kuroki, Machine Translation of JP 2000-248920 A, Sep. 12, 2000.*
European Search Report from related European Patent Appl. No. 05380147.8, mailed Dec. 1, 2006.
European Search Report from related European Patent Appl. No. 07761818.9, mailed Mar. 29, 2010.
European Search Report from related European Patent Appl. No. 07797326.1, mailed Mar. 29, 2010.
Final Office Action from related U.S. Appl. No. 11/204,324, mailed Feb. 13, 2008.
Final Office Action from related U.S. Appl. No. 11/204,324, mailed Oct. 19, 2009.
Final Office Action from related U.S. Appl. No. 11/204,324, mailed Sep. 12, 2008.
International Search Report from International Appl. No. PCT/US07/68132, dated Dec. 4, 2007.
Non-Final Office Action from related U.S. Appl. No. 11/204,324, mailed May 22, 2008.
Non-Final Office Action from related U.S. Appl. No. 11/204,324, mailed May 25, 2007.
Non-Final Office Action from related U.S. Appl. No. 11/204,324, mailed May 7, 2009.
Office Action from related Australian Patent Appl. No. 2007248010, mailed Jan. 14, 2011.
Office Action from related Canadian Patent Appl. No. 2,640,015, mailed Mar. 25, 2011.
Office Action from related Chinese Patent Appl. No. 200780015955.2, mailed Jul. 21, 2010.
Office Action from related Chinese Patent Appl. No. 200780016085.0, mailed Dec. 7, 2010.
Office Action from related New Zealand Patent Appl. No. 571993, mailed Apr. 15, 2010.
Office Action from related New Zealand Patent Appl. No. 571994, mailed Apr. 12, 2010.
Office Action from related U.S. Design U.S. Appl. No. 29/229,913, mailed Jun. 28, 2006.
Office Action from related U.S. Appl. No. 11/743,765, mailed Jan. 28, 2010.
Office Action from related U.S. Appl. No. 11/743,911, mailed May 29, 2009.
Office Action from related U.S. Appl. No. 12/767,180, mailed Nov. 24, 2010.
International Search Report for International Application No. PCT/US07/68097, mailed Feb. 26, 2008; 1 page.

* cited by examiner

DEVICE AND METHOD FOR THE REDUCTION OF EMISSIONS

CROSS-REFERENCE TO RELATED APPLICATIONS

The present application is a continuation patent application, and incorporates by reference, U.S. Utility patent application Ser. No. 11/743,765 filed on May 3, 2007 entitled "Device and Method for the Reduction of Emissions" which claims priority from and incorporates by reference prior U.S. Provisional Patent Application Ser. No. 60/746,341 filed May 3, 2006 in the name of Sergio Varkala Sangiovani, entitled "System and Method for Reduction of Emissions."

BACKGROUND TO THE INVENTION

There is a need for a method and system capable of efficiently and effectively filtering pollutants from exhaust gases. Although there are a number of devices available which are useful for filtering and catalyzing combustion gases or chemical reactions, each of these devices is incapable of providing an effective method for reducing pollutants cost effectively for the reasons described herein. It is generally acknowledged that the functional efficiency of combustion engines is directly related to the engine's ability to discharge gas created during the combustion process. One key element of the efficient discharge of gas is the existence of an adequate amount of counter-pressure at the precise time during the combustion process. This is an issue that has largely been ignored in creating these devices.

In general, an internal engine of combustion operates from the explosion of an air/fuel mixture that causes the expansion of the gases that move the piston of a cylinder. At the end of this cycle, an escape valve opens and the burnt gases are expelled at an extraordinary speed and sound. The performance of a combustion engine is affected by a variety of factors, including the quality of the fuel, pressure under which the fuel ignites, etc.

Because of the importance of relationship between fuel and air in the combustion mixture, the engines in most vehicles or devices are controlled by an electronic injection system. When fuel and air are mixed, the spark plug ignites and causes the explosion that puts into motion some parts of the engine, thus enabling the vehicle or device to move. The result of this "explosion" inside the engine also produces a variety of pollutant gases which are eliminated through the exhaust system. Some of these gases are: water vapor ($H^2O$); carbon dioxide ($CO^2$); nitrogen ($N^2$); carbon monoxide (CO); hydrocarbons (HxCy); nitrogen oxide ($N^2O$); hydrogen (H); methane (CH4); and oxygen ($O^2$). The most toxic gases to human beings are: carbon monoxide (CO) which reduces the oxygenation of the blood, affects the nervous system, worsens cardiac and respiratory illnesses, and can cause fatigue and migraine in low concentrations and death in high concentrations; hydrocarbon (HxCy); and nitrogen oxide ($N^2O$) which affects the lungs and heart, can cause bronchitis, acid deposition and diminishes the atmospheric visibility.

Once a optimal performance of a combustion engine is achieved, the system metrics of the optimal system can be used as a reference against which to measure the effect of various changes to the exhaust system, such as the collector, the catalytic converter, the diameters of the pipe, and the systems for the elimination of noise. By altering characteristics of the system, it is possible to minimize the emission of harmful gases generated during combustion by increasing the periods of low pressure between gas emissions from the explosions.

Besides the production of gases, burning fuel produces material particles (MP) that vary in composition in relation to, among other things, the type of fuel, the quality of the engine maintenance and also in relation to the working temperature of the engine. The material particles are formed from the agglomeration of hydrocarbons that are not combusted and water and impurities of the fuel to the nuclei of chemical carbon element. Material particulates can be inhaled and lodged in deep areas of the human lung, for example, and are widely considered to be an irritating agent for respiratory airways. These particles cause pulmonary illnesses that afflict the elderly and children mainly and in particular during the colder months of the year, when the temperatures are extremely low, a fact that increases the concentration of material particles. This process of contamination increases the cancerous elements that might possibly exist in material particles. It is also important to consider the other undesirable effects in the atmosphere, such as the reduction of visibility and the worsening of the "greenhouse effect".

The material particles generally show a great dimensional variation. This variation causes any type of porous filter to a precocious saturation that, in turn, provokes functional overload to the components of the engine, resulting in an increase of fuel consumption, diminished power of the engine, increase of the volume of gases emitted during the combustion process, increase of temperature, and possible destruction of the engine.

With the knowledge about problems caused by these gases, several components designed to assist in the emission control have been developed. Amongst the most important are electronic control unit ("E.C.U."), the lambda sensor, the EGR valve and the catalytic converter. The control of the air/fuel admission made by the E.C.U. is simply a microcontroller (microprocessor with embedded RAM and ROM memories, wherein the ROM already comes from the factory with specific program recorded on to it) making use of entrances of analog and digital exits, gathering the signals such as temperature and speed obtained from sensors. The E.C.U. searches in its entries for the sensors conditions. The software program recorded in its ROM analyses this data and, according to the programmed information, considers power, economy, and pollution factors to determine and implement the point of work of the valve of shock and the actuator of the impeller.

The lambda sensor is typically located in the exhaust system. It measures the amount of oxygen molecules that have not been consumed in the combustion process and which are therefore expelled together with the combusted gases through the exhaust pipe. This way, the computer will command the injection of more fuel in case there are excess oxygen molecules or, alternatively, to inject less fuel in cases where there are fewer oxygen molecules. By enriching or impoverishing the air/fuel mixture, the engine will work more efficiently, polluting much less, wasting less fuel and with less maintenance. Lambda is the ratio of amount of air available for combustion to the amount of air required for combustion to be stoichiometric. The desired value of lambda is one (1) which indicates that the combustion is perfect.

At the exit of the sensor is an electric signal of a voltage that is proportional to the amount of oxygen in the combusted gases and this voltage, in turn, is proportional to the air/fuel ratio. The ECU controls adjustments in the position of the actuator of the impeller and in the position of the shock valve, resulting in a richer air/fuel mixture (more combustible) or a leaner air/fuel mixture (less combustible). While the engine is warming up, the shock valve is kept partially closed, thereby allowing a richer air/fuel mixture (i.e. more fuel). In the neutral gear, the shock valve is adjusted to a lambda value of 1, while during low speed the impeller is kept partially closed, thus saving in fuel. In the other gears, the ECU shock valve is adjusted according to settings which are adopted to optimize power and economy and minimize pollution. In electronic management, this valve is controlled by the Electronic Control Module which uses actuators to determine the moment and the time where it must operate and its real performance monitored for a present potentiometer in the proper valve. This, in effect, will be part of the subject matter described herein.

The EGR valve controls the flux and the moment where these gases must be absorbed in the combustion chamber. The valve must be open under each of the following conditions: warm engine; rotation of the superior engine to the one of the idling; diverse conditions of acceleration and deceleration of the engine. The amount of the exhaust gases existing in the chamber, and the time that the valve remains open, will depend on the changes in the vacuum and the pressure of the exhaust pipe gases, in accordance with the pattern of the work of the engine. The exhaust gases are a mixture of combusted fuels and, as a result, they are no longer combustible. Moreover, if they occupy too much space in the chamber, they will limit the combustion of the air/fuel mixture, consequently diminishing its temperature. By reducing the temperature, the level of formation of nitrogen oxides produced by the engine is also reduced.

The catalytic converter, located in the exhaust system behind the lambda sensor, functions as a filter that reacts chemically, transforming the harmful gases that still remain in the exhaust stream. Behind the catalytic converter, is the muffler or silencer which must attenuate the sound and dampen the vibrations from the beat of the chain of gases (through bulkheads and with the flux passing through a series of punched pipes and chambers,) absorb the sound waves and control the counter-pressure.

Both the catalytic converter and the muffler are designed to cause a certain counter-pressure in the exhaust system. Without the correct control of the counter-pressure, the exhaust system becomes extremely damaging to the performance of the engine. It will be apparent to those skilled in the art that an engine at optimal performance gets the maximum power from a displacement of the piston, and proper discharge of the exit gases serves to generate maximum power and, therefore, the best performance. A double valve/escape system offers restrictive conditions, creating the counter-pressure.

Even the fuel engine, with the current technology, presents an excess of emissions of gases and material particles in the atmosphere. The ability to get the maximum power and performance is directly linked to the exhaust of the gases from the exhaust pipe. The exhaust process must account for the emission of gases when the engine is running at maximum power. When the engine operates outside of this parameter, resulting in a super dimensioned exhaustion, it will not have the proper restriction of the gases to get the best power and performance from the engine. This causes areas of low pressure resulting in waves of explosion of the gases in the engine causing an unnecessary increase of the emissions of gases and the increase of fuel consumption.

Mercedes-Benz of Brazil has published a report on the development and manufacturing of devices such as filter for material particles entitled "The Commercial Vehicles and the Environment" which verifies much of the foregoing information. Besides this report, it is generally known that a test using a filter of material particles in a fleet of vehicles that circulates in the urban environment was conducted by Mercedes-Benz GAC.—Germany. The filter in this study was made by means of a rolled ceramic wire net in a pipe that, in turn, was installed in the interior of a carcass, which replaces the muffler installed in the exhaust pipe of the automobile. In this configuration, a system of catalytic regeneration is used in the burning of the material particles that are deposited in the filter, keeping the restriction of the gases to the acceptable levels for the current environmental legislation once the device is automatically set in motion during the operation of the automobile.

One device for reducing emissions is described in U.S. patent application Ser. No. 11/204,324 filed Nov. 2, 2005 comprises a metallic cylindrical carcass with bevelled opening in a diagonal line in its posterior part where it is affixed by a clamp to an exhaust system or escape and its anterior part is adapted affix to a metallic capsule. However, this device does not include a fibrous blanket and the corresponding benefits associated therewith.

Despite the promoted efficiency of the methods and systems of the prior art, many are encumbered by high costs of manufacturing and therefore are impracticable from the commercial point of view, particularly for use with existing automobiles.

SUMMARY OF THE INVENTION

The system and method described herein relate to a novel solution for the improved use of fuel and the treatment of gases emitted from combustion engines and, more specifically, the gases that are emitted through exhaust pipes, such as automobile vehicles and industrial equipment. An objective of the present invention is to reduce environmental pollution and, as a result, to improve the conditions of life, including the quality and quantity of the flora and fauna on the planet Earth. The emission of pollutant gases in the atmosphere has significantly contributed to contamination of the environment. There is an overwhelming demand for a solution capable of curbing the alarming effects caused by worldwide environmental degradation.

The present invention provides a variety of ecologic and economic advantages. For example, because the present invention filters particulates and greatly reduces the amount of carbon monoxide, hydrocarbons and other gases produced by the combustion of fuel, this invention has direct effect in the improvement of the environment. This minimizes the damaging effects of the environmental phenomenon known as the "greenhouse effect" and improves the air quality in urban centers.

In one embodiment, the present invention comprises a cylindrical carcass with a beveled opening in a diagonal line in its proximal part. The carcass may be removably attached to an engine's exhaust system. A bobbin is affixed in or to the distal portion of the carcass. A cylindrical-shaped fibrous blanket may be inserted in the carcass and the fibrous blanket may be wrapped in a wire mesh. A second fibrous blanket formed into a cone with the larger diameter of the cone positioned proximally may be removably inserted in the cylindrical-shaped fibrous blanket.

Results from initial tests of one embodiment of the present invention show reduction of approximately 33% of the emission of carbon monoxide and of approximately 43% of the emission of hydrocarbons and particulates, thus resulting in a more efficient use of fuel. In addition it is possible to identify operational advantages, where the application of this invention does not compromise the performance of the combustion engine due to an exclusive constructive concept of a system that reduces the periods of low pressure of the gas exhaustion proceeding from the explosions of the fuel of the combustion engine. The direct implications of these positive characteristics are the reduction of fuel consumption and in the emission of gases. It brings the engine closer to the point of peak performance avoiding overloading its components while working, as it has significant improvement of the burning of the gases of combustion. It also reduces the formation of impurities in the system, thus increasing the time of useful life and minimizing the need of corrective maintenance.

The device also presents advantages from the point of view of the product itself, where the constructive concept shows extreme simplicity and practicality, factors that contribute to the reduction of fixed costs involved in its manufacture and therefore making the final price accessible to the consumer market.

The economic aspect is even more evident when we take into account that the device can be used indefinitely, as it can be washed with anti-grease products, thus eliminating accumulated particles, and yet cleaned in compliance with environmental regulations.

In addition, the invention also reduces the level of noises emitted from the exhaust system by acting as a sound baffle, thereby reducing noise pollution.

For all these reasons, and many others, the device and method of the present invention represents an innovation in the field of emission control.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE EMBODIMENTS

The present invention provides an efficient device and method for reducing the emission of harmful gases in the environment, reducing noise, reducing the consumption of fuel, and improving an engine's performance, all in a cost effective manner. The engine may be any form of combustion engine such as, for example, an engine in a car, truck, lawnmower, or other vehicle or device. The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Figure 1:
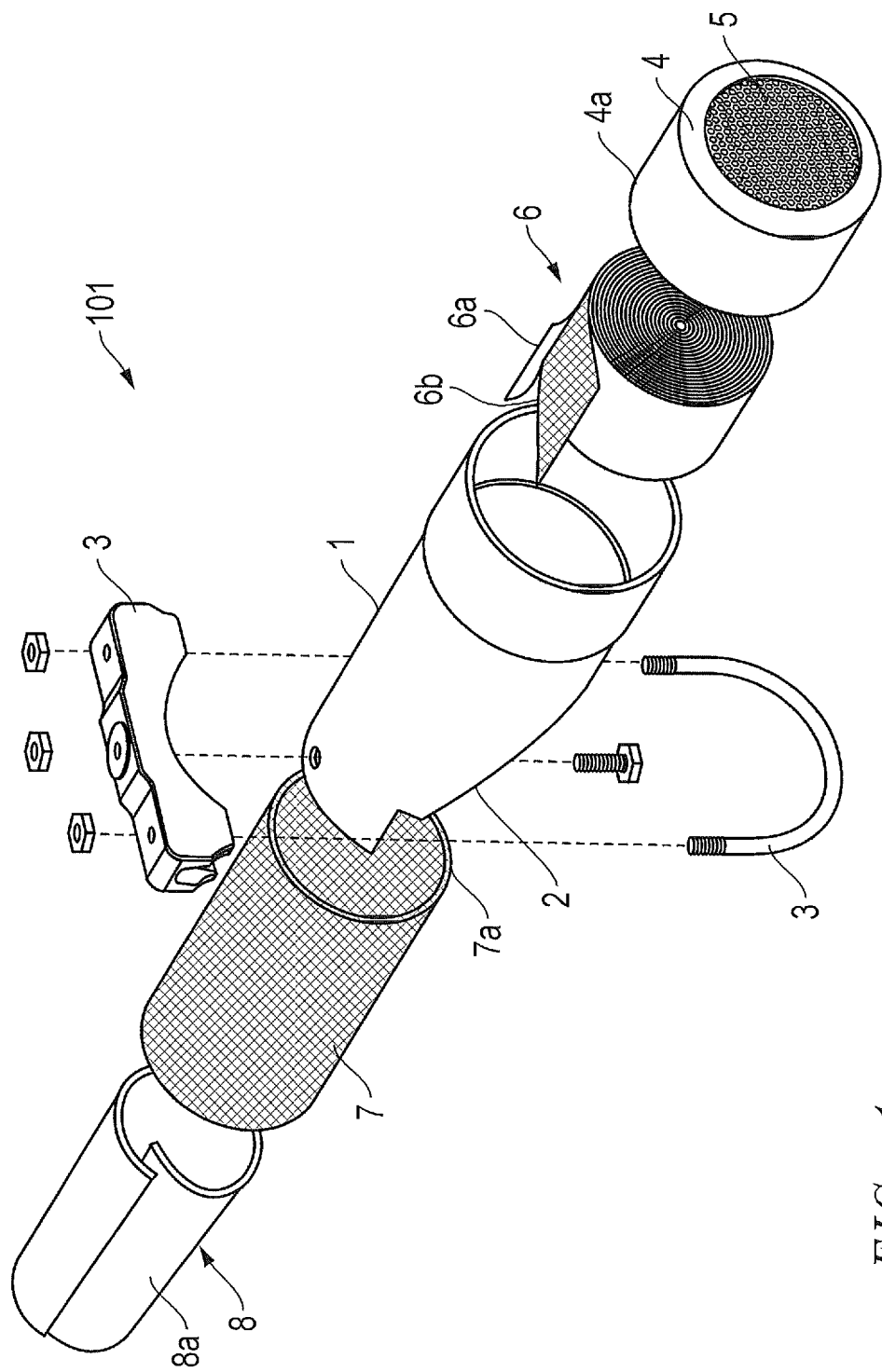
FIG. 1 shows a blown up perspective view of the set of components that compose one embodiment of the device of the present invention.

Referring now to the drawings, FIG. 1 shows one embodiment of the device 101 comprising a cylindrical carcass 1 with a beveled opening 2 in a diagonal line in its proximal part where it is fixed by a clamp 3 for attaching the device 101 to an engine's exhaust system and its frontal part is adapted to receive and to fix a capsule 4. The carcass 1 and the capsule 4 may be made of any material capable of withstanding the heat and pressure of the applications including, for example, aluminum, steel, stainless steel or aluminized steel. The capsule 4 is generally cylindrical with an internal reflux 4a in its frontal part to receive and to fix a screen under pressure 5. The capsule may also have a cylindrical lateral reflux 5a to receive and fix a combination of a bobbin 6 and/or a fibrous blanket cylinder 7. The screen 5 may be metallic such as, for example, a punched metal web or a wire mesh or, alternatively, may be constructed by perforating the material used to construct the capsule. The bobbin 6 may be made of one or more metals or of other materials capable of withstanding the heat and pressure of an exhaust system and may be constructed by wrapping two metal fabrics around a central point.

In another configuration, the carcass 1 and the capsule 4 are integrated together into one cylinder. In this case, the screen may be affixed, or perforations may be made, in the distal end of the cylinder and the bobbin may be placed inside the cylinder at the distal end. By configuring the cylinder in this manner, there is no seam where the carcass 1 and the capsule 4 come together.

In one configuration, the fibrous blanket 7 cylinder is made by wrapping the fibrous blanket in a punched conductive web 6a and/or mesh 6b and overlapping the ends to form a spiral spring. The fibrous blanket 7 may be made of any material which can withstand the heat and pressure of the application. Examples include the combination of one or more of an aramid, a meta-aramid, a polyamide, a polyphenylene sulfide, a p-phenylene-1,3,4-oxadiazole, polytetraflouroethylene, and basalt. In addition, each case where reference is made herein to a fibrous blanket 7, it should be understood that the material may be removed from the carcass for replacement and/or cleaning at any time.

A diaphragm 8 formed by wrapping a fibrous blanket 8a into a cone with the larger radius positioned proximally and the smaller radius positioned distally. In one embodiment of the invention, the fibrous blanket 8a is wrapped in such a manner that the overlapping ends at the narrow end of the cone are secured together and, in another configuration, the overlapping ends at the narrow end of the cone are allowed to overlap but are not secured to one another. The diaphragm 8 may be removably attached to the carcass 1. The diaphragm 8 may be made of any material which can withstand the heat and pressure of the application. Examples include the combination of one or more of an aramid, a meta-aramid, a polyamide, a polyphenylene sulfide, a p-phenylene-1,3,4-oxadiazole, polytetraflouroethylene, and basalt. In addition, each case where reference is made herein to a diaphragm 8, it should be understood that the material may be removed from the carcass for replacement and/or cleaning at any time.

Figure 2:
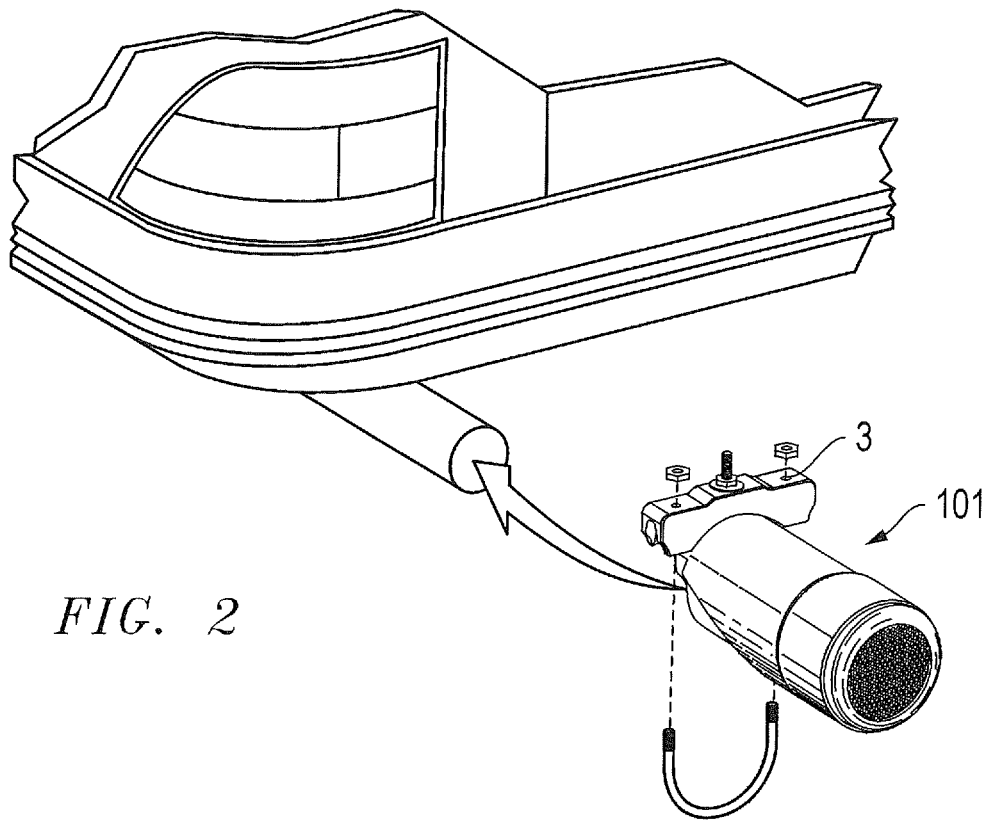
FIG. 2 shows the view representing the attachment of one embodiment of the device to the end of an exhaust system.
Figure 3:
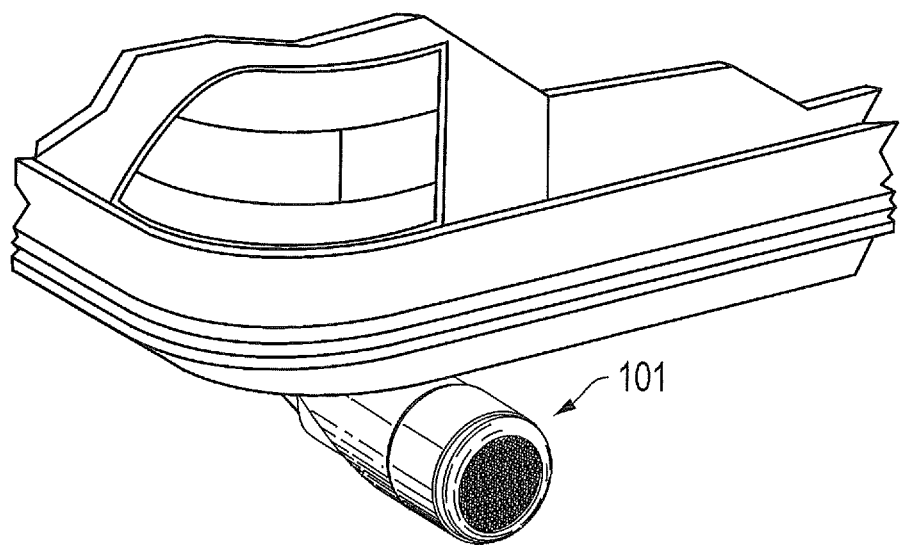
FIG. 3 shows a view of one embodiment of the device installed on the end of an exhaust system.

Once assembled, the proximal end of the carcass 1 is attached to an engine's exhaust system. One manner in which one embodiment of the present invention may be attached to an exhaust system is show in FIGS. 2 and 3. The device may be attached in a variety of ways using a variety of attachment devices known in the art. The device may be either permanently or removably attached to the exhaust system. In the configuration shown in FIGS. 2 and 3, the device is attached using a U-bolt which wraps around the engine's exhaust pipe and through the carcass and is thereafter secured using machine bolts.

The effect produced by each explosion of the fuel in a combustion engine provokes a high-pressure wave of gases (shown in FIGS. 4, 5, 6, 8 and 9) that is sent quickly to the collector. This wave will flow through the exhaust system until being expelled in the atmosphere through the exhaust pipe. Between the serial explosions that transform the chemical energy to mechanical energy, there are periods of low pressure. These periods of low pressure are variable in relation to the rhythm of the explosions. The faster the engine works, the fewer areas of low pressure. One result of the use of this device is the transformation of these variable periods of low pressure into small constant periods. As a result, the exhaust system is able to produce the necessary counter-pressure for better use in the system involving valves, gas escape, and fuel injection. The result is the reduced emission of gases and reduced fuel consumption.

Figure 4:
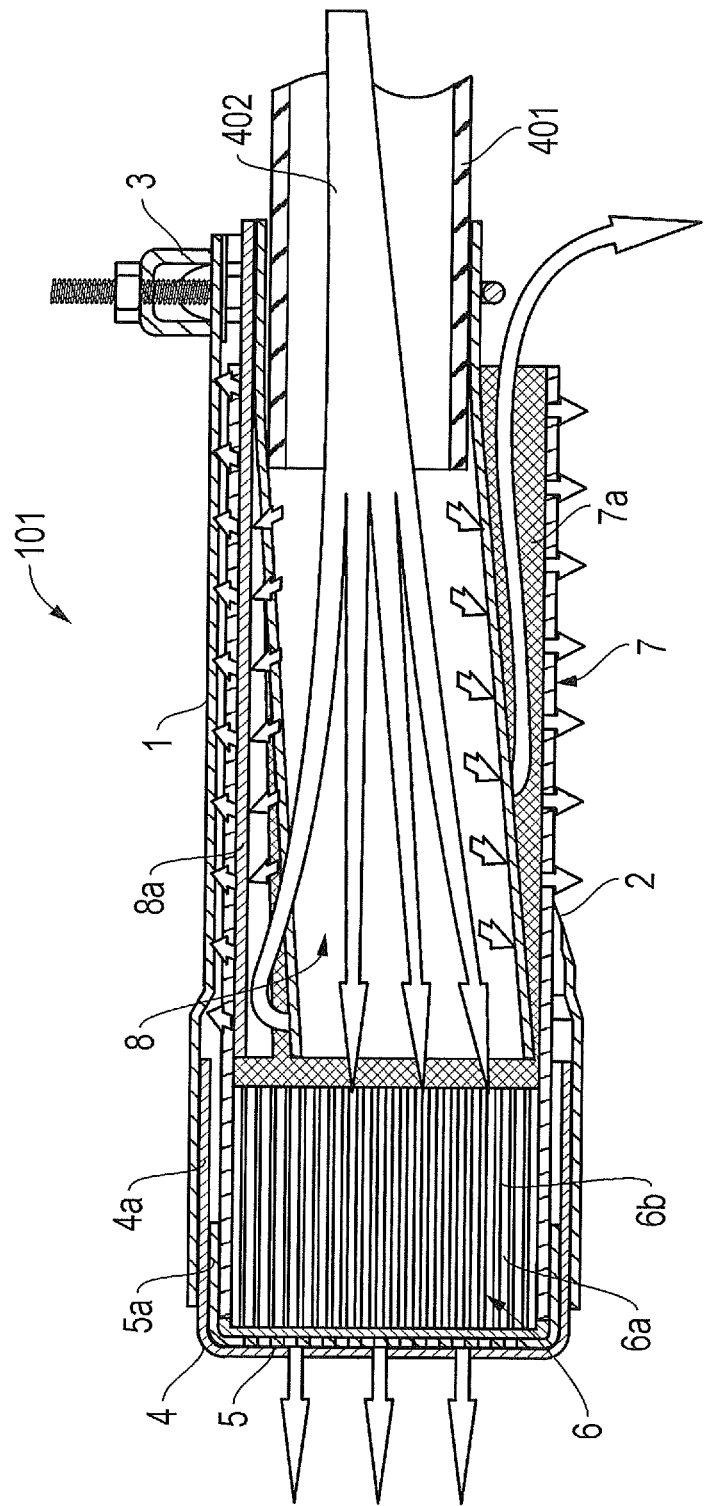
FIG. 4 shows a side cut view of one embodiment of the device, indicating the flow of the gas waves proceeding from the engine's exhaust system.

As shown in FIG. 4, the gas 402 leaves the exhaust pipe 401 and enters the proximal end of the device 101. In the illustrated embodiment, the gas flows first through the diaphragm 8 and, because the diaphragm is formed into a conical shape in such a manner that a portion of the gas 402 is allowed to escape through the side of the diaphragm 8 because, as discussed above, the sides of the diaphragm 8 may not be secured together. Some portion of the gas 402 also passes through the diaphragm whereupon particulates in the gas 402 are removed and the cleaned gas escapes into the atmosphere. Finally, a portion of the gas proceeds past the distal end of the diaphragm 8 and enters the proximal end of the bobbin 6.

Figure 5:
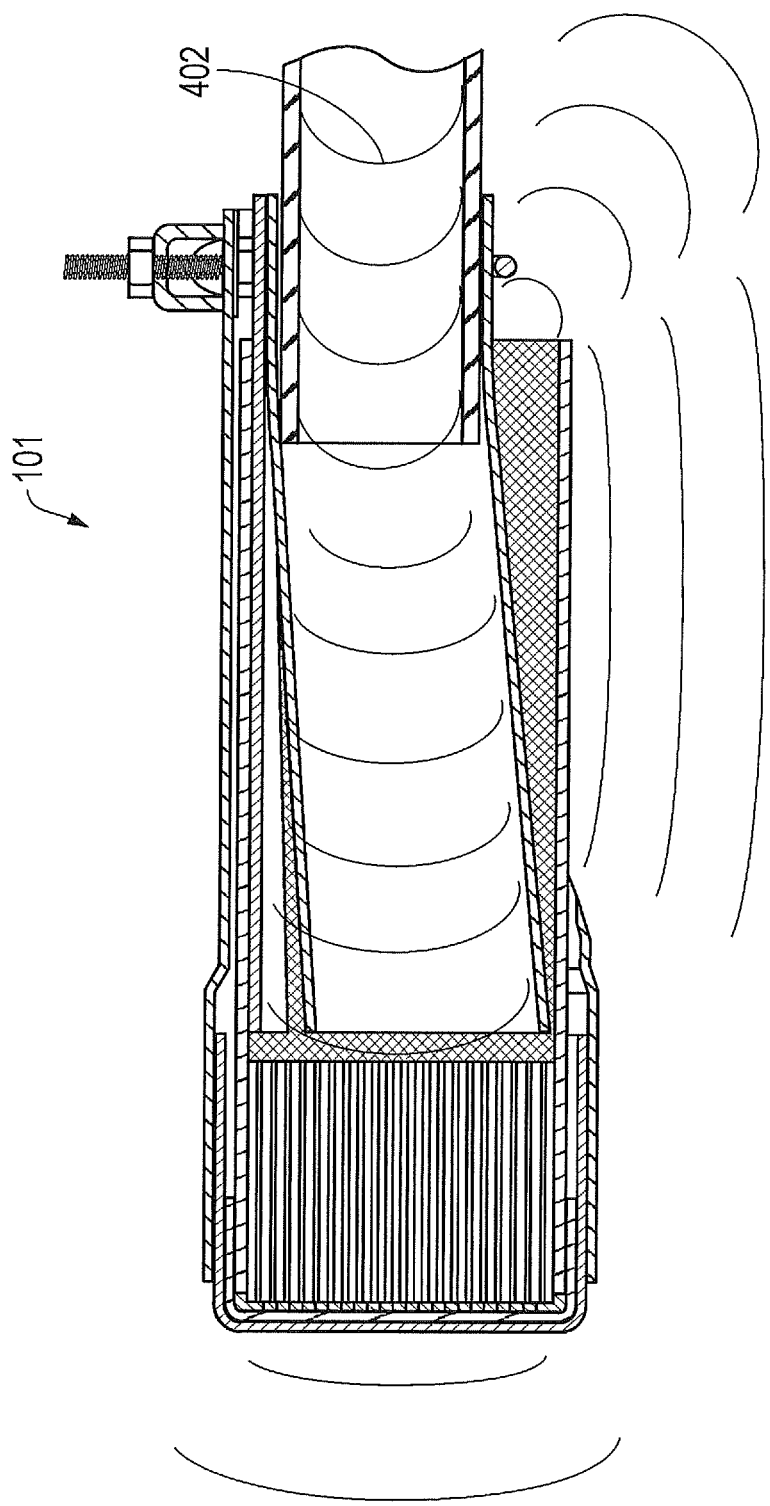
FIG. 5 shows a side cut view of one embodiment of the device, indicating the behavior of the gas waves proceeding from the engine's exhaust system.

FIG. 5 shows a side cut view of one embodiment of the device, indicating the flow of the gas waves proceeding from the engine's exhaust system. The serial explosions that transform the chemical energy to mechanical energy, there are periods of low pressure. These periods of low pressure are variable in relation to the rhythm of the explosions.

Figure 6:
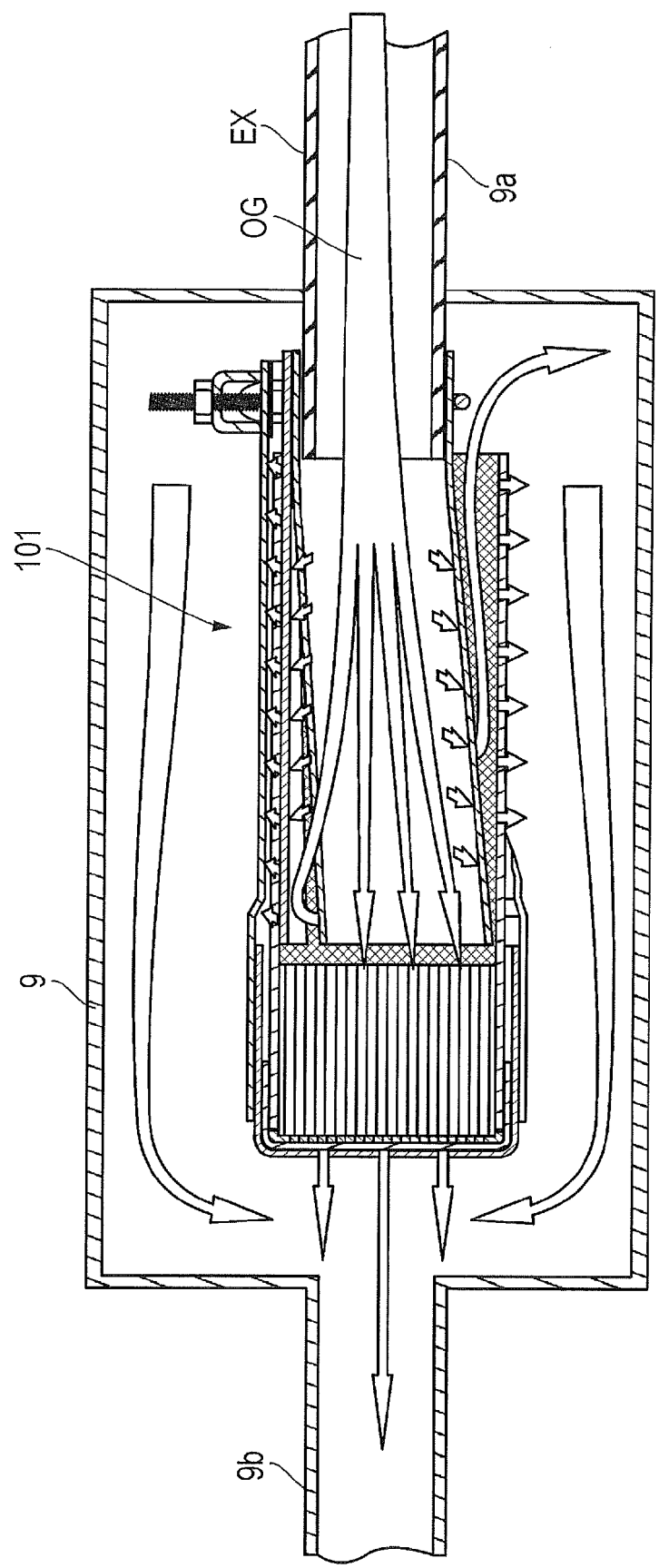
FIG. 6 shows an interior side cut view of one embodiment of the device inside the carcass of the exhaust system indicating the flow of the gas waves.
Figure 7:
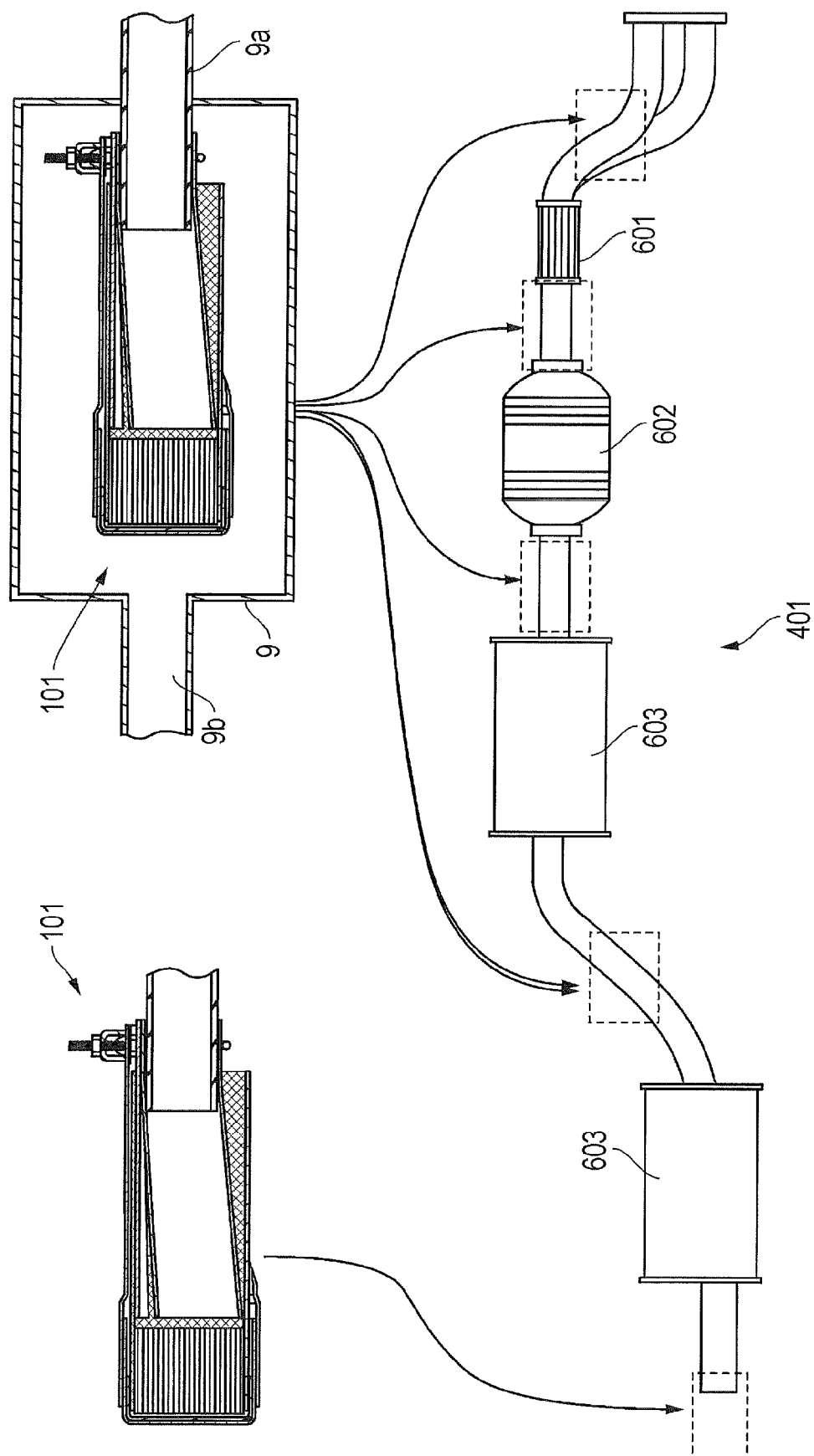
FIG. 7 shows alternate ways of applying one embodiment of the device in an engine's exhaust system.
Figure 8:
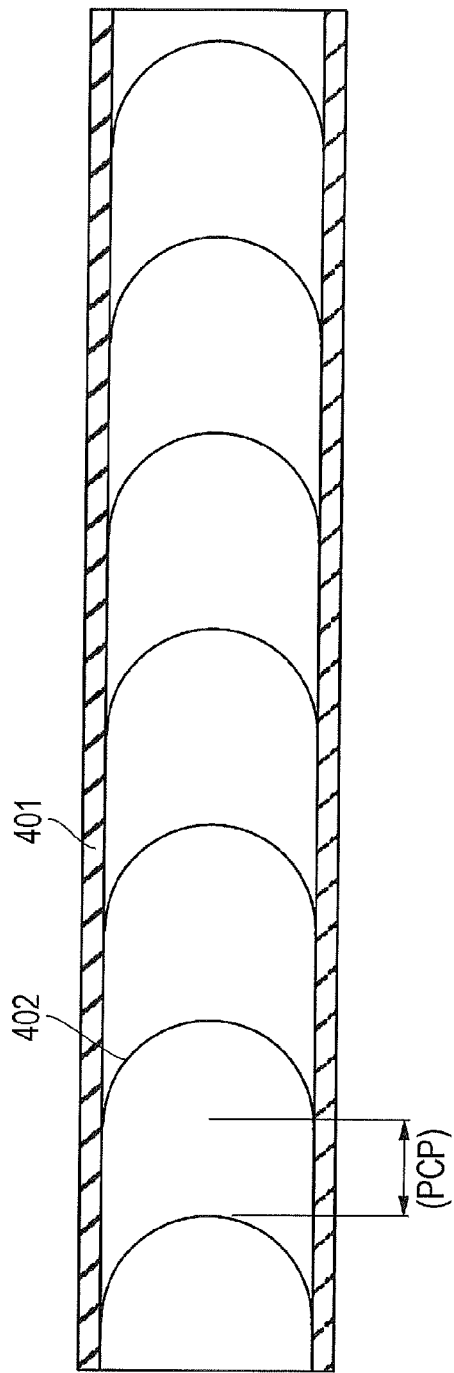
FIG. 8 shows a representation of the gas waves originated from the exhaust system without the device of the present invention.
Figure 9:
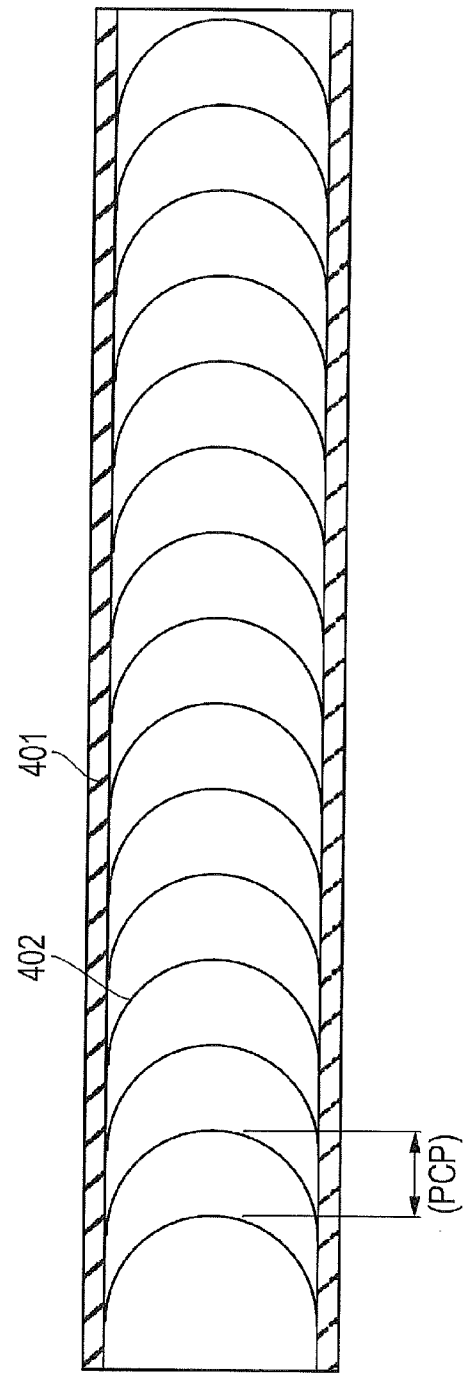
FIG. 9 shows a representation of the gas waves originated from the exhaust system with the device of the present invention.

As illustrated in FIG. 6 and FIG. 7, the device 101 carries through various functions in its operation, being able to be installed in any part of the exhaust system, meaning, after the collector 601, or before, of the catalytic converter 602, or before, of after the muffler 603, or intercalated or later. In short, the efficacy of the device of the present invention does not depend on the positioning inside the exhaust system.

So that the device 101 can be installed in the various parts of the exhaust system as described in the paragraph above and illustrated in FIG. 6 and FIG. 7, in an alternative embodiment the device 101 is installed internally to a lodging carcass 9, endowed with entrance 9a and exit 9b for the gas 402. Its functioning depends on the combustion engine to be working and emitting gas 402 to create the explosions. Periods of low pressure (LP) are produced during low rotation of the engine. When gas 402 enters the device 101 the amplitude is reduced by the conical configuration of the diaphragm 8, this effect reduces the potential energy of the gas 402, reduces its speed, distributes it across the area impacted by the gas 402 in the bobbin 6, and spreads the energy of shock of the wave 402 across the bobbin 6.

The bobbin 6 causes a restriction in the flow of the gas 402 thereby restricting the necessary compression to reduce the periods of low pressure (LP) between the waves of gas 402. This effect causes a chain of events in the waves of gas 402 during exhaust, reducing the periods of low pressure (LP) between the waves. By increasing the speed of the cycle of the explosions, the pressure of the waves 402 on the diaphragm 8 and on the bobbin 6 increases. The increase of the pressure on the walls of the diaphragm 8 causes the fibers to allow a bigger gas outflow between them, balancing with the elastic energy of the fibrous material thereby regulating the excess of the counter-pressure returned to the system. The increase of the cycle of the explosions also increases the waves of shocks on the bobbin 6 by the energy stored from its spring effect. When the bobbin is configured by wrapping two metals together, the energy of the shock waves of gas 402 causes the bobbin 6 to move in the opposite direction to its mechanic memory, thereby producing a bigger gap between its parallel segments and regulating the counter-pressure with the increase of the permission of flow of the gas waves 402. With the energy in the shock of the wave, the elastic energy of the bobbin 6 increases, and the bobbin allows greater gas flow between coated plates in a circular movement. Once the balance of the bobbin 6 is reestablished it returns to its initial configuration.

When the speed of the explosions reach the point when periods of low pressure (LP) are de minimus, it causes the counter-pressure offered by the diaphragm 8, in the overlapping of the material in its conical form, to be moved allowing extra flow of gases, thereby normalizing the counter-pressure of the exhaust system. When moving to the overlapping of the material of the diaphragm 8 it offers a radial increase of the proximal side of the cone, having its maximum opening limited by the fibrous blanket 7. This causes the waves of gases 402 to be radially shocked against the walls of the fibrous blanket 7, allowing a regulable counter-pressure in relation to the gases that enter its walls and in relation to the forced passage until the exit of the gases. The metallic carcass 1 concentrates and directs the exit of the gases through its exit in diagonal cut 2 directed towards the ground. This effect produces a controllable counter-pressure in the exhaust system taking advantage of the system of exhaust versus valves, resulting in improvement in the engine's performance and reducing the consumption of fuel.

Both the bobbin and the fibrous blanket 6 and 7 that are part of the device 101 act as material particle filters. In the bobbin 6, the gathering of material particles is accomplished by the collection of shock of particles in the walls of the mesh of the fibrous blanket 7a and of the bobbin 6b. The particles agglutinate as a result of the lost of speed and due to their own physical characteristics. The fibrous blanket 7 and 8a collects material particles that do not pass through the material. These two systems of gathering of material particles are efficient and can be cleaned and reused.

The bobbin 6 may be constructed using different metals, such as aluminum, zinc, copper, iron and others, to generate an electric or voltage differential that makes available ions to the system. These ions generated in the bobbin 6 affect the catalytic capacity in the gases emitted in the fuel engines at low temperatures, or until the end of the process of catalyses of gases initiated in the catalytic system of the fuel engines that, due to the speed of the waves 402 in the exhaust system, did not provide enough time to conclude the necessary catalytic reactions, or even when there is deactivation, for diverse reasons (temperature, contamination of the oil of the engine, excess of SO2) in the catalytic converter.

Another important effect is the reduction of the sound emitted from the device resulting from the dampening of the shockwaves of gases against the bobbin 6 and the fibrous blankets 7*a* and 8*a*.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of possible filters, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

The invention claimed is:

1. A device for reducing emissions comprising:
   a carcass defining a distal end and a proximal end, wherein said proximal end is affixed to an exhaust outlet of a combustion engine system;
   a capsule affixed to said distal end of said carcass, wherein said capsule has a screen positioned at said capsule's distal end;
   a bobbin positioned within said capsule; and
   a fibrous blanket that is positioned inside said carcass to remove particles from exhaust gas expelled through said exhaust outlet, wherein said fibrous blanket is removably positioned inside said carcass to enable said fibrous blanket to be removed from said carcass after said fibrous blanket accumulates said particles.

2. The device of claim 1 further including a diaphragm wherein said diaphragm is formed into a cone.

3. The device of claim 1, wherein said carcass is made of aluminum, steel, aluminized steel, or stainless steel.

4. The device of claim 1, wherein said bobbin is constructed by wrapping two fabrics of different metal around a central point.

5. The device of claim 1, wherein said carcass is removably affixed to said exhaust outlet.

6. The device of claim 1, wherein said fibrous blanket is made of one or more of an aramid, a meta-aramid, a polyamide, a polyphenylene sulfide, a p-phenylene-1,3,4-oxadiazole, polytetraflouroethylene, and basalt.

7. The device of claim 1, wherein said exhaust gas enters said device subsequent to exiting a muffler, such that said exhaust outlet is downstream in said exhaust system from said muffler.

8. The device of claim 1, wherein at least some of said exhaust gas is expelled through a portion of said proximal end of said carcass.

9. The device of claim 8, wherein at least some of said exhaust gas is expelled through said bobbin.

10. The device of claim 1 further comprising a second fibrous blanket affixed to a conductive mesh.

11. The device of claim 10, wherein said conductive mesh is positioned around the perimeter of said fibrous blanket.

12. The device of claim 1 further including a diaphragm wherein said diaphragm is formed into a cone and said diaphragm is positioned inside said carcass.

13. The device of claim 12 wherein said diaphragm is made of one or more of an aramid, a meta-aramid, a polyamide, a polyphenylene sulfide, a p-phenylene-1,3,4-oxadiazole, polytetraflouroethylene, and basalt.

14. The device of claim 12 wherein said diaphragm is removable affixed to said carcass.

15. A method for reducing emissions comprising:
    affixing a proximal end of a carcass to an exhaust outlet of a combustion engine system, wherein a capsule is positioned at a distal end of said carcass with a bobbin positioned within said capsule and a screen positioned at said capsule's distal end, a fibrous blanket is positioned inside said carcass to remove particles from exhaust gas expelled through said exhaust outlet, and said fibrous blanket is removably positioned inside said carcass to enable said fibrous blanket to be removed from said carcass after said fibrous blanket accumulates said particles.

16. The method of claim 15 further including providing a diaphragm wherein said diaphragm is formed into a cone.

17. The method of claim 15, wherein said carcass is made of aluminum, steel, aluminized steel, or stainless steel.

18. The method of claim 15, wherein said bobbin is constructed by wrapping two fabrics of different metal around a central point.

19. The method of claim 15, wherein said carcass is removably affixed to said exhaust outlet.

20. The method of claim 15, wherein said fibrous blanket is made of one or more of an aramid, a meta-aramid, a polyamide, a polyphenylene sulfide, a p-phenylene-1,3,4-oxadiazole, polytetraflouroethylene, and basalt.

21. The method of claim 15, wherein affixing said proximal end of said carcass to said exhaust outlet comprises enabling at least some of said exhaust gas to be expelled through a portion of said proximal end of said carcass.

22. The method of claim 21, wherein affixing said proximal end of said carcass to said exhaust outlet comprises enabling at least some of said exhaust gas to be expelled through said bobbin.

23. The method of claim 15 further comprising providing a second fibrous blanket affixed to a conductive mesh.

24. The method of claim 23, wherein said conductive mesh is positioned around the perimeter of said fibrous blanket.

25. The method of claim 15 further including positioning inside said carcass a diaphragm wherein said diaphragm is formed into a cone.

26. The method of claim 25 wherein said diaphragm is made of one or more of an aramid, a meta-aramid, a polyamide, a polyphenylene sulfide, a p-phenylene-1,3,4-oxadiazole, polytetraflouroethylene, and basalt.

27. The method of claim 25 wherein said diaphragm is removably affixed to said carcass.

* * * * *

UNITED STATES PATENT AND TRADEMARK OFFICE
CERTIFICATE OF CORRECTION

Page 1 of 1

PATENT NO.      : 8,474,250 B2
APPLICATION NO. : 12/845345
DATED           : July 2, 2013
INVENTOR(S)     : Sergio Varkala Sangiovani It is certified that error appears in the above-identified patent and that said Letters Patent is hereby corrected as shown below:

<u>Title page,</u> Related U.S. Application Data

"(63) Continuation of application No. 11/743,765, filed on May 3, 2007, now abandoned." should read -- (63) Continuation of application No. 11/743,765, filed on May 3, 2007, now abandoned.

(60) Provisional application No. 60/746,341, filed on May 3, 2006. --.

Signed and Sealed this
Fourteenth Day of January, 2014

Michelle K. Lee
*Deputy Director of the United States Patent and Trademark Office*